(12) United States Patent
Medina-Martinez et al.

(10) Patent No.: US 12,033,727 B2
(45) Date of Patent: Jul. 9, 2024

(54) MANAGING AND ACCESSING EXPERIMENT DATA USING REFERENTIAL INDENTIFIERS

(71) Applicant: MEMORIAL SLOAN KETTERING CANCER CENTER, New York, NY (US)

(72) Inventors: Juan Santiago Medina-Martinez, New York, NY (US); Elli Pappaemmanuil, New York, NY (US); Andrew Kung, New York, NY (US); Juan Esteban Arango Ossa, New York, NY (US); Max Fine Levine, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 178 days.

(21) Appl. No.: 17/629,292

(22) PCT Filed: Jul. 23, 2020

(86) PCT No.: PCT/US2020/043257
§ 371 (c)(1),
(2) Date: Jan. 21, 2022

(87) PCT Pub. No.: WO2021/016448
PCT Pub. Date: Jan. 28, 2021

(65) Prior Publication Data
US 2022/0246245 A1      Aug. 4, 2022

Related U.S. Application Data

(60) Provisional application No. 62/877,724, filed on Jul. 23, 2019.

(51) Int. Cl.
*G06F 16/00* (2019.01)
*G06F 16/22* (2019.01)
(Continued)

(52) U.S. Cl.
CPC ......... *G16B 50/30* (2019.02); *G06F 16/2264* (2019.01); *G06F 16/955* (2019.01)

(58) Field of Classification Search
CPC .................................................. G06F 16/955
See application file for complete search history.

(56) References Cited

U.S. PATENT DOCUMENTS

| 2002/0049782 A1 | 4/2002 | Herzenberg et al. |
| 2006/0074953 A1 | 4/2006 | Dettinger et al. |

(Continued)

OTHER PUBLICATIONS

International Search Report and Written Opinion on PCT/US2020/043257 dated Oct. 16, 2020.

*Primary Examiner* — Ajith Jacob
(74) *Attorney, Agent, or Firm* — Foley & Lardner LLP

(57) ABSTRACT

The present disclosure is directed to managing and accessing experiment data. A data processing system may generate a system identifier for each instance that leads to a generation of experiment data. A first segment may refer to a source entity, and may be used to differentiate identifiers generated by different source entities. This implementation may aim to provide an explicit representation of the data generation process while providing a glimpse on select metadata attributes, such as an individual species, sample class, and experimental technique used to generate the dataset. These constraints may prevent duplicates and may enable system-side associations among subjects, samples, aliquots, and experiments.

20 Claims, 11 Drawing Sheets

(51) Int. Cl.
 *G06F 16/955* (2019.01)
 *G16B 50/30* (2019.01)

(56) References Cited

U.S. PATENT DOCUMENTS

| | | | |
|---|---|---|---|
| 2012/0145778 A1* | 6/2012 | Cong | G07C 9/27 707/E17.014 |
| 2016/0378916 A1 | 12/2016 | Drmanac et al. | |
| 2017/0199967 A1 | 7/2017 | De La Torre-Bueno | |

* cited by examiner

700A

705 — Individual IID_H100554 [X]

710 — IID_H100554 RL_fltaml_009
Individual RL_fltaml_009 | Species HUMAN
+ add individual tags!

715 — Samples
IID_H100554 ● — 730

720 — ANALYSES EXPERIMENTS DETAILS
Analyses

| Key | Status | Name | Version | Assembly | Application | Target Experiments | Reference Experiments |
|---|---|---|---|---|---|---|---|
| 1934 | SUCCEEDED | PINDEL | 1.5.4 | GRCh37 | 6 | I-H-100554-T4-1-D1-1 | I-H-100554-N1-1-D1-1 |
| 1936 | SUCCEEDED | PINDEL | 1.5.4 | GRCh37 | 6 | I-H-100554-T3-1-D1-1 | I-H-100554-N1-1-D1-1 |
| 1938 | SUCCEEDED | PINDEL | 1.5.4 | GRCh37 | 6 | I-H-100554-T2-1-D1-1 | I-H-100554-N1-1-D1-1 |

3 ▸ Showing 1-3 of 67 analyses

725 — Projects

| Key | Title | Group | Principal Investigator | Owner | Analyst Coordination |
|---|---|---|---|---|---|
| 102 | FLT3 ITD AML responders non-responders | CHM | PI_ABC@ex_inst.org | OW@ex_inst.org | PI_ABC@r ... PI_ABC@r |

3 ▸ Showing 1-1 of 1 projects

FIG. 7A

MANAGING AND ACCESSING EXPERIMENT DATA USING REFERENTIAL INDENTIFIERS

CROSS REFERENCE TO RELATED APPLICATIONS

The present application is a U.S. National Phase Application under 35 U.S.C. § 371 of International Application No. PCT/US2020/043257, filed Jul. 23, 2020, which claims priority to and the benefit of U.S. Provisional Application No. 62/877,724, titled "Using a Dynamic Tree Visualization Within an Application to Retrieve Patient Data and Metadata," filed Jul. 23, 2019, each of which is incorporated herein by reference in its entirety.

BACKGROUND

A biological sample may be obtained from a specimen or subject in a controlled environment for evaluation and experimentation. Various types of data regarding the biological sample may be collected in accordance with various bioinformatics techniques.

SUMMARY

Various types of data may be generated by performing experiments on aliquot (e.g., technical replicates) that are obtained from a biological sample of a subject. The experiments may include, for example, imaging (e.g., radiology, histopathology, microscopy), sequencing testing (e.g., (e.g., whole genome sequencing, whole exome sequencing, targeted Deoxyribonucleic acid (DNA) sequencing, targeted ribonucleic acid (RNA) sequencing, and whole transcriptome), genetic diagnostic testing (e.g., for disease-related genotypes, karyotypes, mutation types, and phenotypes), and non-diagnostic testing (e.g., forensic and paternity testing), among others. Performing such experiments may yield various types of information in regards to the aliquot and the biological sample under evaluation.

A massive amount of data may be gathered and aggregated from the multitude of experiments performed by different vendors on various aliquots obtained from several subjects. A database management system (DBMS) may be used to store and maintain the experiment datasets. The DBMS may generate an index to identify a particular experiment dataset maintained on the database. For example, the DBMS may index the datasets using one or more tables on the database using a row index value and a column index value to uniquely identify a location of a particular experiment dataset within the tables. Under a key-value schema, the row index value in which the dataset is located may be used as the key, and one or more of the fields of the dataset as the value. Subsequently, a combination of the row index value and the column index value or key-value pair in a query may be used to search the database and retrieve the experiment dataset therefrom.

These approaches to indexing, however, may impose a number of restrictions on the types of data. For example, when a new dataset is acquired, the DBMS may perform normalization on the dataset before insertion and storage onto the database. The datasets may have been generated by different vendors in accordance to a format or protocol particular to one vendor. Without any standardization, the various functions of the DBMS with respect to the data, such as insertion, storage, identification, and retrieval, may be severely hampered. In addition, such indexing approaches may not leverage the particularities of datasets acquired from experiments, leading to suboptimal storage, identification, and retrieval on the database. For example, when multiple datasets are acquired from a single subject, sample, or aliquot, there may be similar metadata describing the subject, sample, or aliquot in connection with the experiment data. The arrangement of the resultant datasets in the database may be such that the locations are concentrated in one section of the database (e.g., in a handful of rows in the table), resulting in $O(n)$ insertion, search, and retrieval. Furthermore, the indices created by the DBMS to identify individual datasets may be arbitrary or opaque, and not readily be understood to a user of the database. This reduces the accessibility and usability of the datasets of the database, thereby leading to a decrease in the quality of human-computer interactions (HCl) between the user and the database.

To address these and other technical challenges, a records management system may generate a system identifier for each instance that leads to a generation of experiment data. A first segment may refer to a source entity (sometimes herein referred to as an institution or an instance), and may be used to differentiate identifiers generated by different source entities. This implementation may aim to provide an explicit representation of the data generation process while providing a glimpse on select metadata attributes, such as an individual species, sample class, and experimental technique used to generate the dataset. These constraints may prevent duplicates and may enable system-side associations among subjects, samples, aliquots, and experiments.

In generating and configuring the system identifiers, the schema may take into account the attributes related to the creation of the experiment dataset. The attributes may include: the source entity that generated the experiment dataset; the subject from which the biological sample for the experiment was collected; the biological sample from which the aliquot is obtaine, the aliquot upon which the experiment is performed; and the experiment dataset itself, among others. By leveraging these attributes, the records management system may generate corresponding segments for the system identifier. One or more of the segments may cumulatively refer to one of the attributes related to the dataset. For example, in the system identifier, a first segment may refer the source entity; a second segment, together with the previous segment, may refer to the subject; a third segment, together with the previous segments, may refer to the sample; a fourth segment, together with the previous segments, may refer to the aliquot; and the fifth segment, together with all the previous segments, may refer to experiment itself.

Using the system identifiers, the record management system may maintain and arrange the experiment datasets on the database. The system identifiers and the datasets accessible via the identifiers may also be visualized or presented as graph representation (also referred herein as a dynamic tree). The graph representation may have nodes and edges to represent the associations among the datasets on the database. The nodes of the graph representation may be arranged in levels corresponding to the different attributes. Across successive levels, the graph representation may have additional nodes as the more specific attributes may have greater variance. For example, a graph representation may be generated for a single subject. From the subject, multiple biological samples may be obtained; for each sample multiple aliquots may be taken; for each aliquot, various experiments may be performed. The record management system may present the graph representation via a user interface, which may be navigated to provide specific data regarding individual nodes.

By leveraging the attributes across experiment datasets in this manner, the record management system may provide for instantaneous (e.g., O(1) time) insertion, search, and retrieval of datasets. Since the indexing is independent of the formatting of the datasets, the record management system may store and maintain the data from different vendors without data normalization, thereby saving computing resource entities. Due to the format and structure of the system identifiers, the record management system may prevent (or make less likely) concentration of datasets in a particular section of the database. In addition, the format and structure of the segments within the system identifier may also allow users to easily read and deduce which particular source entity, subject, biological sample, aliquot, and experiment an individual dataset refers to. Having a whole-picture view of assets related to a subject may provide a significant insight in the context of precision medicine and multi-modal digital representations of a subject across locality and time. With this insight, the quality of HCI between the user and the system may be greatly improved.

At least one aspect is directed to systems and methods of maintaining experiment data. A data processing system may have one or more processors coupled with memory. The data processing system may maintain a database in accordance with a plurality of system identifiers. Each system identifier of the plurality of system identifiers may have a plurality of segments for a corresponding plurality of attributes. Each of the plurality of segments in each system identifier may include a first segment to reference an instance corresponding to a source entity; a second segment, with the first segment, to reference a subject; a third segment, with the first segment and the second segment, to reference a biological sample acquired from the subject; a fourth segment, with the first segment, the second segment, and the third segment, to reference an aliquot corresponding to at least a portion of the biological sample; and a fifth segment, with the first segment, the second segment, the third segment, and the fourth segment, to reference a dataset of an experiment performed on the aliquot of at least the portion of the biological sample that is acquired from the subject.

In some embodiments, the data processing system may receive, from a data acquirer associated with the source entity, the dataset of the experiment performed on the aliquot obtained from at least the portion of the biological sample of the subject. In some embodiments, the data processing system may determine, responsive to receipt of the dataset of the experiment and subsequent to generation of a first system identifier having a first attribute, that a second attribute including at least one of the source entity, the subject, the biological sample, or the aliquot upon which the experiment is performed corresponds to the first attribute of the first system identifier. In some embodiments, the data processing system may generate, responsive to the determination, a second system identifier for a record including the dataset of the experiment based on the first system identifier. At least a portion of the second system identifier may match a corresponding portion of the first system identifier.

In some embodiments, the data processing system may determine that a first attribute of a first system identifier including at least one of the source entity, the subject, the biological sample, or the aliquot corresponds to a second attribute of the dataset of the experiment for a second system identifier. In some embodiments, the data processing system may identify, from the plurality of segments of the first system identifier, one or more segments corresponding to the first attribute determined to correspond to the second attribute. In some embodiments, the data processing system may assign the one or more segments of the first system identifier to corresponding one or more segments of the second system identifier to associate the first system identifier with the second system identifier.

In some embodiments, the data processing system may maintain a plurality of counters for the corresponding plurality of attributes. The plurality of attributes may include the source entity, the subject, the biological sample, and the aliquot. In some embodiments, the data processing system may determine, responsive to receipt of the dataset of the experiment, that a first attribute of a first system identifier including at least one of the source entity, the subject, the biological sample, or the aliquot corresponds to a second attribute of the dataset of the experiment for a second system identifier. In some embodiments, the data processing system may identify, responsive to the determination, a counter from the plurality of counters for the first attribute determine to correspond to the second attribute. In some embodiments, the data processing system may assign, using the counter, the fifth segment of the second system identifier for the dataset of the experiment.

In some embodiments, the data processing system may determine, responsive to receipt of the dataset of the experiment, that a plurality of attributes identified by a first system identifier including at least one of the source entity, the subject, the biological sample, the aliquot, and the dataset, matches a plurality of attributes derived from the dataset. In some embodiments, the data processing system may restrict, responsive to the determination, generation of a second system identifier for the dataset using the plurality of attributes derived from the dataset of the experiment.

In some embodiments, the data processing system may receive, from a client device, a query for records identifying one or more attributes of a plurality of attributes. The plurality of attributes may include the source entity, the subject, the biological sample, the aliquot, and the experiment. In some embodiments, the data processing system may provide, from a plurality of records maintained on the database, a subset of records corresponding to the one or more attributes as identified in the query for records to the client device.

In some embodiments, the data processing system may provide a graph element using at least one of the plurality of system identifiers. The graph element may include a plurality of nodes and a plurality of edges to connect the plurality of nodes. The plurality of nodes may correspond to a plurality of attributes. The plurality of edges may correspond to associations among the plurality of attributes. In some embodiments, at least one of the plurality of segments in each system identifier may include a marker of a plurality of markers and a unique value. The plurality of markers may indicate a condition for a corresponding attribute.

At least one aspect is directed to systems and methods of accessing experiment data. A data processing system may have one or more processor coupled with memory. The data processing system may generate, using a plurality of system identifiers for a corresponding plurality of records that are maintained on a database, a graph element. The graph element may include a first level having a first node, the first node corresponding to a subject common to the plurality of records as indicated by a first segment of each of the plurality of system identifiers; a second level having a second set of nodes, each of the second set of nodes corresponding to a aliquot for at least one record of the plurality of records as indicated by the first segment and a second segment of at least one corresponding system identifier of the plurality of system identifiers; a first set of edges between each of the second set of nodes of the second level to the first node of the first level, each edge of the first set of edges indicating that the aliquot is obtained from the subject; a third level having a third set of nodes, each of the third set of nodes corresponding to an experiment performed on the aliquot of a corresponding record of the plurality of records as indicated by the first segment, the second segment, and a third segment of a corresponding system identifier of the plurality of system identifiers; and a second set of edges between each of the third set of nodes of the third level and a corresponding node in the second set of nodes of the second level, each edge of the second set of edges indicating that the experiment is performed on the corresponding aliquot. The data processing system may provide the graph element on a user interface for presentation.

In some embodiments, the data processing system may identify, from each of the plurality of system identifiers, a plurality of attributes including the subject, the aliquot, and the dataset of the experiment. In some embodiments, the data processing system may generate, based on the plurality of attributes, the first node of the first level, the second set of nodes of the second level, and the third set of nodes of the third level.

In some embodiments, the data processing system may identify, from among the plurality of records, a first set of associations between aliquots for at least a first subset of the plurality of records and the subject. In some embodiments, the data processing system may identify, from among the plurality of records, a second set of associations between datasets of the experiment for at least a second subset of the plurality of records and the aliquots. In some embodiments, the data processing system may generate the first set of edges based on the first set of associations. In some embodiments, the data processing system may generate the second set of edges based on the second set of associations.

In some embodiments, the data processing system may monitor, via the user interface, an interaction with a node from the first node, the second set of nodes, and the third set of nodes of the graph element. In some embodiments, the data processing system may provide, responsive to detection of the interaction with the node, a user element including information on the node. In some embodiments, the data processing system may maintain the plurality of records on the database in accordance with the plurality of system identifiers. Each system identifier of the plurality of system identifiers may have a plurality of segments for a corresponding plurality of attributes. In some embodiments, the user interface may include a plurality of elements corresponding to a plurality of attributes across the plurality of records used to generate the graph element.

BRIEF DESCRIPTION OF THE DRAWINGS

The objects, aspects, features, and advantages of the disclosure will become more apparent and better understood by referring to the following description taken in conjunction with the accompanying drawing, in which:

FIG. 7A-C are illustrations of example user interfaces in response to user interactions in accordance with an illustrative embodiment;

Figure 1:
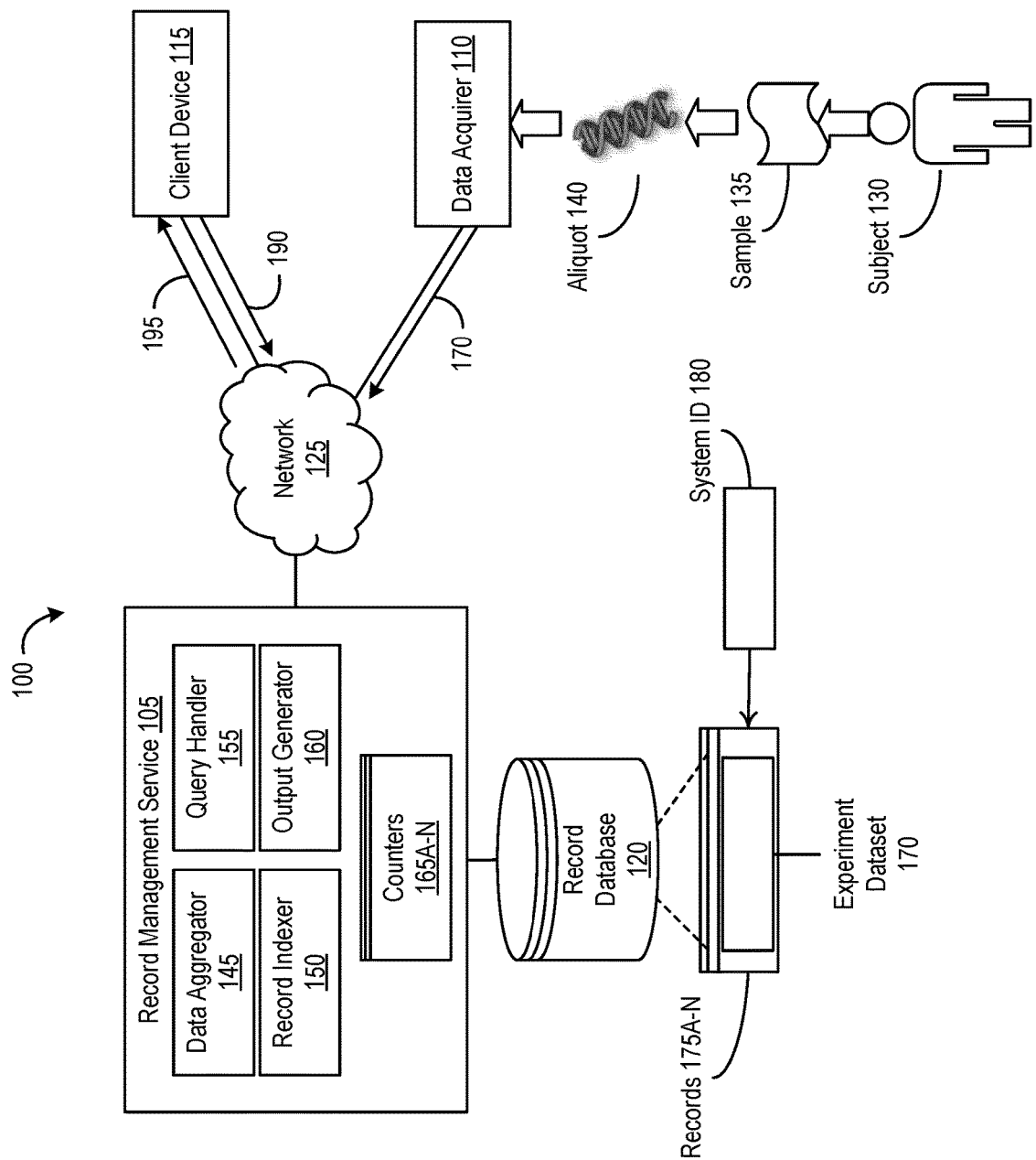
FIG. 1 is a block diagram of a system for maintaining and accessing experiment data in accordance with an illustrative embodiment.

The drawings are not necessarily to scale; in some instances, various aspects of the subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION

Following below are more detailed descriptions of various concepts related to, and embodiments of, systems and methods for maintaining and accessing experiment data. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

Section A describes systems and methods of maintaining and accessing experiment data; and Section B describes a network environment and computing environment which may be useful for practicing various embodiments described herein.

A. Systems and Method of Maintaining and Accessing Experiment Data

Referring now to FIG. 1, depicted is a block diagram of an environment or a system 100 maintaining and accessing experiment data. In brief overview, the system 100 may include at least one records management service 105 (sometimes referred herein as a data processing system), at least one data acquirer 110, at least one client device 115, and at least a record database 120 (sometimes herein referred generally as a database) communicatively coupled with one another via at least one network 125. The records management service 105 may include at least one data aggregator 145, at least one record indexer 150, at least one query handler 155, at least one output generator 160, and a set of counters 165A-N among others. Each of the modules, units, or components in system 100 (such as the records management service 105 and its components, the data acquirer 110, the client device 115, and the network 125, among others)

may be implemented using hardware or a combination of hardware and software as detailed herein in Section B.

In further detail, the data acquirer 110 may obtain, identify, or generate at least one experiment dataset 170. The experiment dataset 170 may have been generated from performing at least one evaluation on at least one aliquot 140 (or other biological material) that is obtained from at least one biological sample 135 of a subject 130. The subject 130 may be any animal from which the biological sample 135 is obtained, such as a human (e.g., as depicted), monkey, pig, bird, chinchilla, rabbit, mouse, cat, dog, cow, and alligator, among others. The biological sample 135 may be obtained from any portion from the subject 130, such as an organ tissue, outer skin, cheek, bodily fluids, bone marrow, buccal swabs, cell lines, and organoids, among others. The aliquot 140 may include or correspond to any genetic material (or any other biological material) acquired from the biological sample 135 of the subject 130, and may include, for example, a DNA analyte. In some embodiments, the data acquirer 110 itself may be associated with a source entity. The source entity may correspond or include a testing institution (e.g., a hospital, clinic, test center, university, research group, or research center).

To generate the experiment dataset 170, the data acquirer 110 (or another computing device) may run or perform the evaluation on the aliquot 140 or on the biological sample 135. The evaluation may include, for example, imaging (e.g. radiology, histopathology, microscopy), sequencing testing (e.g., whole genome sequencing, whole exome sequencing, targeted Deoxyribonucleic acid (DNA) sequencing, targeted ribonucleic acid (RNA) sequencing, and whole transcriptome), genetic diagnostic testing (e.g., for disease-related genotypes, karyotypes, mutation types, and phenotypes), and non-diagnostic testing (e.g., forensic and paternity testing), among others. The experiment dataset 170 acquired from performing the evaluation may include, for example, BAM files, FASTQ files, images, text files, DICOM images, among others. In some embodiments, the data acquirer 110 may facilitate the running of the evaluation on the aliquot 104. For example, a clinician (or another technician) may perform at least a portion of the evaluation, such as obtaining the biological sample 135 itself. In turn, the data acquirer 110 may perform another portion of the evaluation, such as by performing pattern recognition techniques to detect genomic sequences. In some embodiments the data acquirer 110 may display or present an interface for entry of the experiment dataset 170.

In generating, the data acquirer 110 may create or generate metadata associated with the evaluation for the experiment dataset 170. The metadata may identify, indicate, or include various attributes in connection with the experiment dataset 170: the source associated with the acquirer 110 (e.g., name of institution); the subject 130 (e.g., a pseudonym or other identifier, species, gender); the biological sample 135 (e.g., location on body, collection date, associated disease); the aliquot 140 obtained from the biological sample 135; and the experiment itself (e.g. experimental technique, instrument used, instrument manufacturer), among others. In some embodiments, the data acquirer 110 may apply a file format or protocol in generating the experiment dataset 170. The format or protocol may also be applied by the data acquirer 110 to the metadata associated with the experiment dataset 170. The format or protocol may differ among the data acquirers 110 that are to provide the experiment datasets 170.

With generation, the data acquirer 110 may provide, send, or transmit the experiment dataset 170 via the network 125 to the records management service 105. The experiment dataset 170 may be sent in the form of a file, such as in comma separated values (CSV) format, text file format, rich text format, extensible markup language (XML) format, images, sequencing formats, among others. In some embodiments, the data acquirer 110 may transmit the experiment dataset 170 one-by-one to the records management service 105. For example, upon completion of the evaluation of the aliquot 140, the data acquirer 110 may generate and send over the corresponding experiment dataset 170 to the records management service 105. In some embodiments, the data acquirer 110 may transmit the experiment dataset 170 in batches to the records management service 105. The transmission in batches may be in accordance with a delivery schedule. For example, at the scheduled time, the data acquirer 110 may provide all the experiment datasets 170 generated since the previous transmission to the records management service 105. In some embodiments, the data acquirer 110 may send, provide, or transmit the metadata associated with the experiment dataset 170. The metadata may be included in the experiment dataset 170 itself (e.g., in a portion of the same file) or in conjunction with the experiment dataset 170 (e.g., in a separate file).

The data aggregator 145 executing on the records management service 105 may retrieve, identify, or receive the experiment dataset 170 from the data acquirer 110. The experiment dataset 170 may be received with the associate metadata form the data acquirer 110. In some embodiments, the data aggregator 145 may receive the experiment dataset 170 individually one-by-one from the data acquirer 110. In some embodiments, the data aggregator 145 may receive the experiment datasets 170 in batches from the data acquirer 110. In some embodiments, the data aggregator 145 may fetch or retrieve the experiment dataset 170 from one or more of the data acquirers 110. For example, the data aggregator 145 may present an interface that provides a list of data acquirers from which to retrieve experimental data. Upon selection of the interface, the data aggregator 145 may send a request for data to the selected data acquirers 110, and receive the experiment datasets 170. In some embodiments, upon receipt of each experiment dataset 170, the data aggregator 145 may identify the source data acquirer 110 that sends the experiment dataset 170. For example, the data aggregator 145 may identify a source network address (e.g., Internet Protocol (IP) address) from the transmission of the experiment dataset 170. Based on the source network address, the data aggregator 145 may identify the data acquirer 110.

Using the one or more received experiment datasets 170, the data aggregator 145 may create or generate a set of records 175A-N (hereinafter generally referred to as a record 175) to store and maintain on the record database 120. Each record 175 may correspond to a unit of storage in the record database 120 that references, holds, or includes the experiment dataset 170. The data aggregator 145 may configure or generate the record 175 to identify, contain, or otherwise include the corresponding experiment dataset 170. Upon receipt from the data acquirer 110, the data aggregator 145 may instantiate the record 175 to be stored on the record database 120. The data aggregator 145 may insert or include the experiment dataset 170 into the record 175. The inclusion into the record 175 may be agnostic to the formatting of the experiment dataset 170 as defined by the acquirer 110. In some embodiments, the data aggregator 145 may also include the metadata associated with the experiment dataset 170 into the record 175. In some embodiments, the data aggregator 145 may maintain the association between the experiment dataset 170 and the metadata as received from the data acquirer 110.

The record indexer 150 executing on the records management service 105 may maintain the records 175 on the records database 120 in accordance with system identifiers 180. To maintain, the record indexer 150 may determine or generate at least one system identifier 180 for each record 175. The generation of the system identifier 180 may be in response to generation of the record 175. The record indexer 150 may use at least some of the metadata associated with the experiment dataset 170 to generate the system identifier 180. The system identifier 180 may be used to index or identify the record 175 and the experiment dataset 170 of the record 175 stored and maintained on the record database 120.

Figure 2:
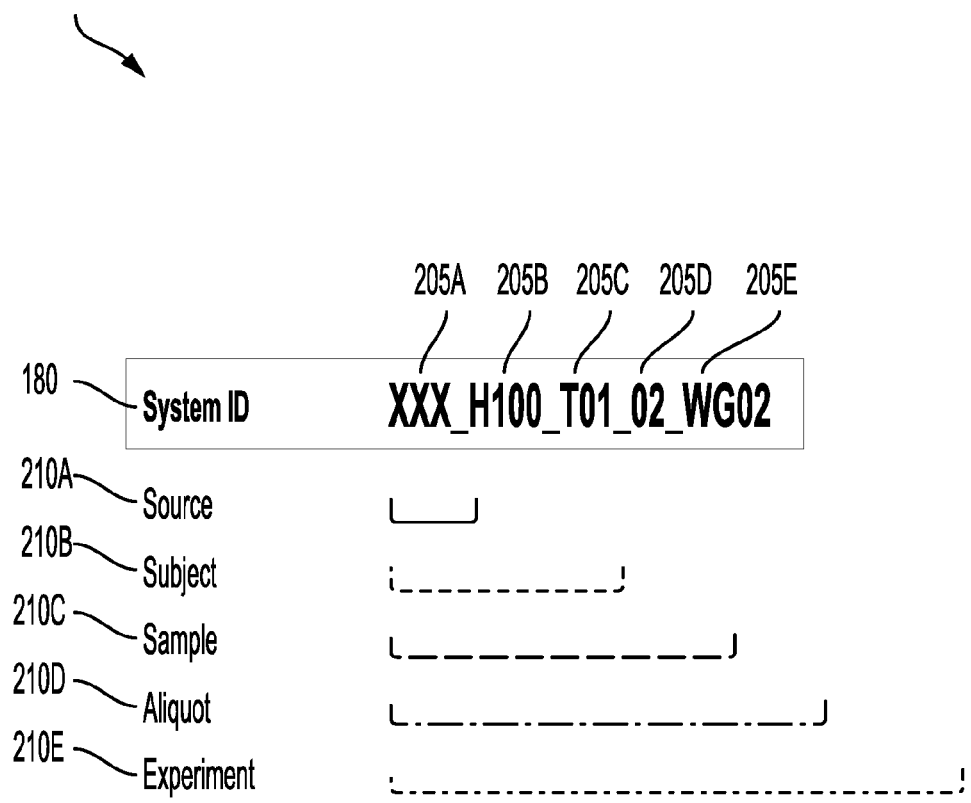
FIG. 2 is a schematic diagram of associations in an example system identifier used to maintain a database in the system for maintaining and accessing experiment data in accordance with an illustrative embodiment.

Referring now to FIG. 2, depicted is a schematic diagram of associations 200 in an example system identifier 180 used to maintain the database 120 in the system 100 for maintaining and accessing experiment data. As depicted, the record indexer 150 may generate the system identifier 180 to include a set of segments 205A-E (hereinafter generally referred to as segments 205). Each segment 205 may correspond to one of a corresponding set of attributes 210A-E (hereinafter generally referred to as attributes 210). The attributes 210 may be obtained or identified from the metadata associated with the experiment dataset 170 referenced by the system identifier 180. For each system identifier 180, there may be any number of attributes 210 used to generate the system identifier 180. For example as depicted, the first attributes 210A may be the source entity (sometimes herein referred to as an instance), the second attribute 210B may be the subject 130, the third attribute 210C may be the biological sample 135, the fourth attribute 210D may be the aliquot 140, and the fifth attribute 210E may be the experiment. Each attribute may correspond to a level of detail. The level of detail in order from descending to ascending may be, for example, source entity, subject 130, biological sample 135, aliquot 140, and the experiment dataset 170 itself.

In the system identifier 180, each attribute 210 may be identified or referenced by one or more of the segments 205 (e.g., in accordance with the associations 200). In some embodiments, cumulative combinations of segments 205 may reference the attributes 210. For example as depicted, the first segment 205A ("XXX") may reference the first attribute 210A corresponding to the source entity; the second segment 205B in combination of the first segment 205A ("XXX_H100") may reference the second attribute 210B corresponding to the subject; the third segment 205C ("XXX_H100_T01") in combination with the first segment 205A and the second segment 205B may reference the third attribute 210C corresponding to the biological sample; the fourth segment 205D in combination with the first segment 205A, the second segment 205B, and the third segment 205C ("XXX_H100 T01_02") may reference the fourth attribute 210D corresponding to the aliquot; and the fifth segment 205E, in combination with the first segment 205A, the second segment 205B, the third segment 205C, and the fourth segment 205D ("XXX_H100 T01_02_WG02"), may reference the fifth attribute 210E corresponding to the experiment.

Figure 3:
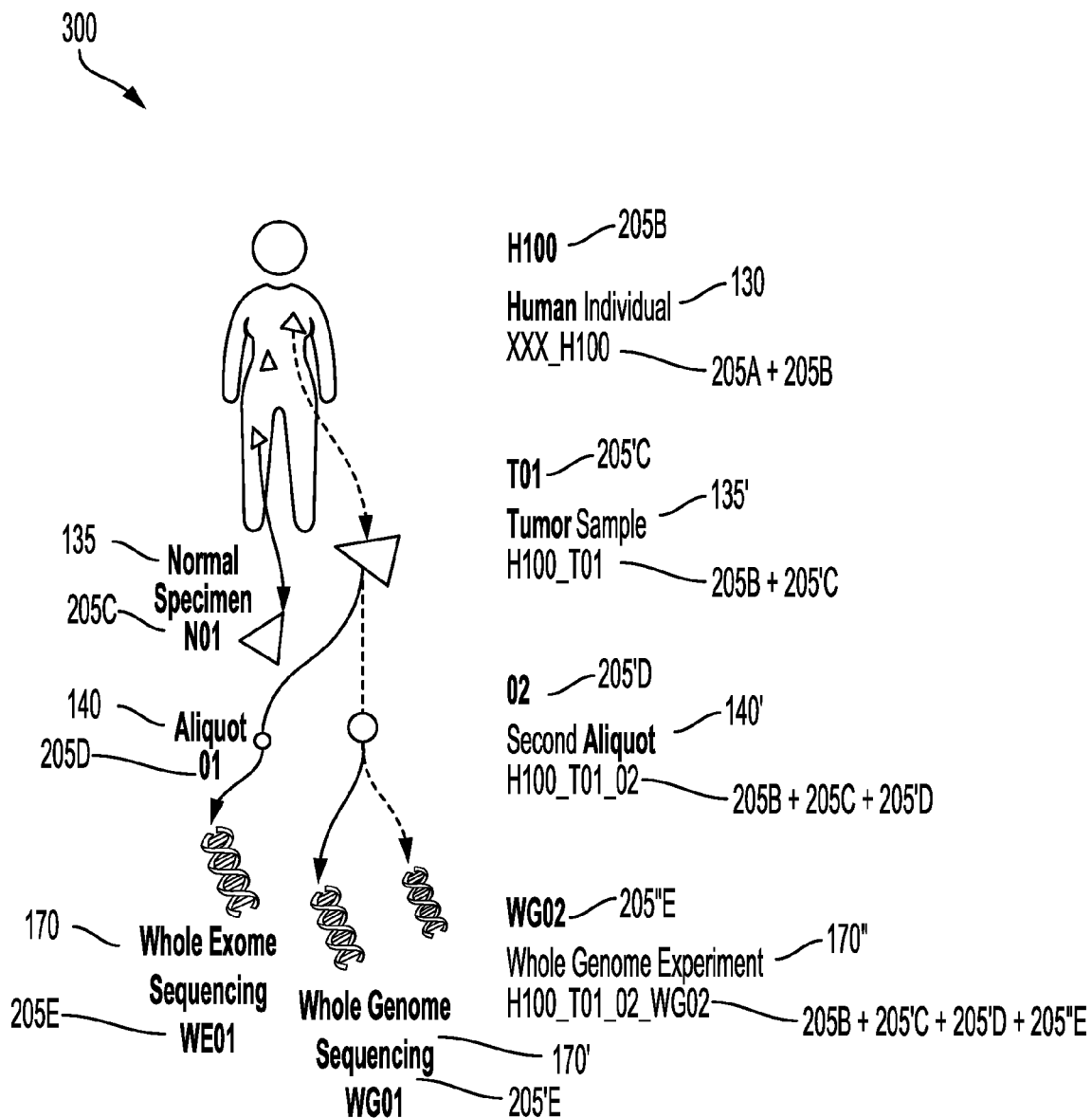
FIG. 3 is a block diagram of associations between segments of a system identifier and corresponding attributes in accordance with an illustrative embodiment.

Referring now to FIG. 3, depicted is a block diagram of associations 300 between the segments 205 of the system identifier 180 and the corresponding attributes 210. As illustrated, the segments 205 of the system identifier 180 may be configured or assigned to indicate that for a single subject 130, multiple samples 135 and multiple aliquots 140 may be obtained that are used to perform various evaluations. For instance, from a single subject 130 (e.g., a human individual), multiple samples 135 and 135' (e.g., a normal specimen and a tumor sample) may be obtained. Using which multiple aliquots 140 and 140' may be acquired that may undergo multiple evaluations from which a corresponding number of experiment datasets 170, 170', 170" (e.g., "whole exome sequencing," "whole genome sequencing," and "whole genome experiment") may be derived. The record indexer 150 may determine and assign individual segments 205 of the system identifier 180 to indicate the multiplicity of biological samples 135, aliquots 140, and the experiments performed thereon. The system identifiers 180 generated for the three experiment datasets 170, 170', and 170" may have common attributes 210 and thus some of the same segments 205, because the experiments are performed on the same subject 130.

As illustrated, the record indexer 150 may generate system identifiers 180 with the first segment 205A and the second segment 205B ("XXX_H100") to reference the subject 130 ("Human individual"). Since experiment datasets 170A-C are from the same subject 130, the first segment 205A and the second segment 205B of corresponding system identifiers 180 generated by the record indexer 150 may be assigned the same attributes 210A and 210B. Moving on, the record indexer 150 may generate the system identifiers 180 with the second segment 205B and the third segment 205'C ("H100_T01") to reference the biological sample 135' ("Tumor Sample") from the subject 130. The second segment 205B and the third segment 205C may be the same for the first experiment dataset 170, the second experiment dataset 170', and the third experiment dataset 170", as all are performed on the same biological sample 135'. However, the second segment 205B and the third segment 205C of the system identifier 180 for whatever experiment is performed on the biological sample 135 ("Normal Specimen") may differ from the experiments performed on the biological sample 135'.

In addition, the record indexer 150 may generate the system identifiers 180 with the second segment 205B, the third segment 205'C, and the fourth segment 205'D ("H100_T01_02") to reference the aliquot 140' ("Second aliquot"). The second segment 205B, the third segment 205C, and the fourth segment 205D may be the same for the second experiment dataset 170' and the third experiment dataset 170", as the experiments are performed on the same aliquot 140'. On the other hand, the second segment 205B, the third segment 205C, and the fourth segment 205D of the system identifier 180 for the first experiment dataset 170 may differ from the other two, as the experiment is performed on a different aliquot 140 ("Aliquot 01").

The record indexer 150 may generate the system identifier 180 with the second segment 205B, the third segment 205'C, the fourth segment 205'D, and the fifth segment 205"E ("H100_T01_02 WG02") to reference the third experiment dataset 170" ("Whole Genome Experiment"). The fifth segment 205"E ("WG02") may be unique to the third experiment dataset 170", and may differ from the fifth segment 205E for the first experiment dataset 170 and the fifth segment 205'E for the second experiment dataset 170'. The fifth segment 205'E ("WG01") of another system identifier 180 may reference the second experiment dataset 170' ("Whole Genome Sequence") performed using also the second aliquot 140'. Likewise, the fifth segment 205E ("WE01") of another system identifier 180 may reference the first experiment dataset 170 ("Whole Exome Sequencing") performed on the first aliquot 140.

Figure 4:
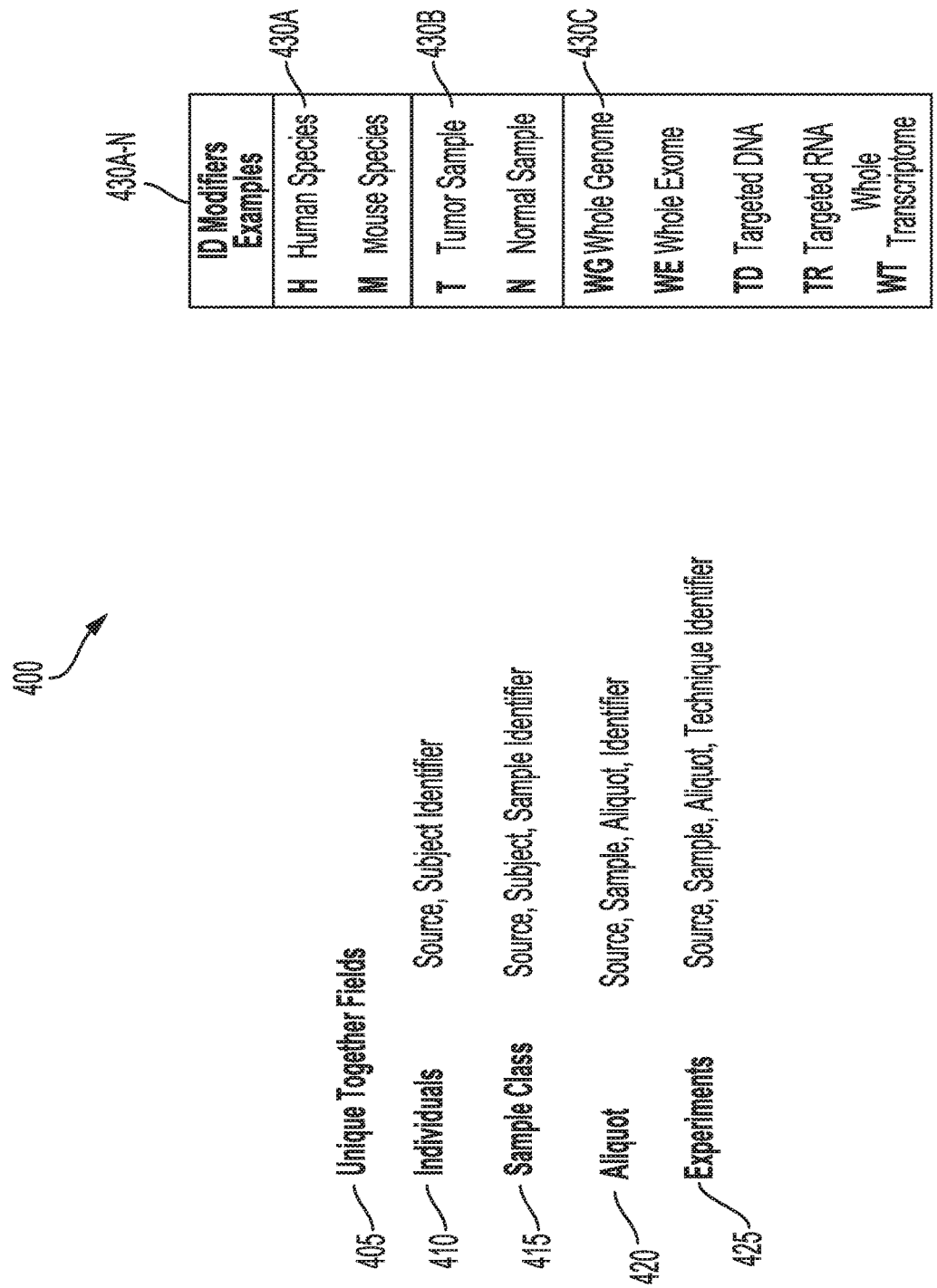
FIG. 4 is a block diagram of associations among fields within segments of a system identifier and corresponding attributes in accordance with an illustrative embodiment.

Referring now to FIG. 4, depicted is a block diagram of associations 400 among fields within the segments 205 of the system identifier 180 and the corresponding attributes 210. As illustrated, the record indexer 150 may generate the system identifier 180 with common segments 205 (or unique-together fields 405) based on common attributes 210. When the subject 130 (or the individual 410) is the same, the record indexer 150 may generate the system identifier 180 to include the same first segment 205A (source identifier) and the second segment 205B (subject identifier). When the biological sample 135 (or the sample class 415) is the same, the record indexer 150 may generate the system identifier 180 to include the same first segment 205A (source identifier), the second segment 205B (subject identifier), and the third segment 205C (sample identifier). When the aliquot 140 (or aliquot 420) is the same, the record indexer 150 may generate the system identifier 180 to include the same first segment 205A (source identifier), the second segment 205B (subject identifier), the third segment 205C (sample identifier), and the fourth segment 205D (aliquot identifier). When the experiment dataset 170 (or experiment) is the same, the record indexer 150 may generate the system identifier 180 to include the same first segment 205A (source identifier), the second segment 205B (subject identifier), the third segment 205C (sample identifier), the fourth segment 205D (aliquot identifier), and the fifth segment 205E (technique identifier).

In some embodiments, the record indexer 150 may generate the system identifier 180 to include one or more modifiers (sometimes herein referred to as markers) from a set of modifiers 430A-N (hereinafter generally referred to as modifiers 430). The modifiers 430 may lend to the legibility or comprehensibility of the user of the system identifier 180 used to index the records 175 maintained and stored on the record database 120. The modifiers 430 in the segments 205 may indicate a condition for the corresponding attributes 210. In some embodiments, the record indexer 150 may assign the modifiers to one or more of the segments 205 in the system identifier 180 based on the attributes 210. For example as depicted, for the second segment 205B to reference the subject 130, the record indexer 150 may insert or include a modifier 430A in the second segment 205B to indicate whether the subject 130 is a human species ("H") or a mouse species ("M"), among others. For the third segment 205C to reference the biological sample 135, the record indexer 150 may insert or include a modifier 430B in the third segment 205C to indicate whether the biological sample 135 is a tumor sample ("T") or a normal sample ("N"), among others. Furthermore, for the fifth segment 205E to reference the specific experiment dataset 170, the record indexer 150 may insert or include a modifier 430C in the fifth segment 205E to indicate whether the experiment performed on the aliquot 140 is a whole genome sequencing ("WG"), whole exome sequencing ("WE"), targeted DNA sequencing, targeted RNA sequencing, or whole transcriptome evaluations, among others.

Upon receipt of the experiment dataset 170, the record indexer 150 may parse the associated metadata to extract, retrieve, or identify the set of attributes 210 (e.g., the source entity, the subject 130, the biological sample 135, the aliquot 140, and the experiment). The identified attributes 210 may be in the form of alphanumeric characters. The record indexer 150 may compare the set of attributes 210 from the received experiment dataset 170 with the corresponding set of attributes 210 of experiment datasets 170 in the records 175 on the database 120. In some embodiments, for each attribute 210 identified, the record indexer 150 may generate a corresponding segment 205. The record indexer 150 may compare the segments 205 generated from the attributes 210 of the newly received experiment dataset 170 with corresponding segments 205 of the experiment datasets 170 in the records 175. Based on the comparison, the record indexer 150 may determine whether at least one of the attributes 210 from the received experiment dataset 170 correspond to (e.g., match) the corresponding attributes 210 of the experiment datasets 170 of the records 175. In some embodiments, the record indexer 150 may perform the determination by comparing the segments 205 derived from the received experiment dataset 170 with the segments 205 of the experiment datasets 170 in the records 175 stored and maintained on the database 120.

The record indexer 150 may determine none of the attributes 210 from the received experiment dataset 170 corresponds to the corresponding attributes 210 in any of the stored experiment datasets 170 of the records 175 based on the comparison. In response, the record indexer 150 may generate new system identifier 180 for the record 175 that is to include the received experiment dataset 170. In generating the system identifier 180, the record indexer 150 may generate at least one segment 205 to differ from the other system identifiers 180 for records 175 of experiment datasets 170 already on the database 120. For example, the record indexer 150 may generate a new value for the first segment 205A referencing the source entity for the new system identifier 180 to reference the record 175 of the newly received experiment dataset 170. In some embodiments, the record indexer 150 may use one or more of the counters 165 to generate the new system identifier 180 as described herein below.

On the other hand, the record indexer 150 may determine one or more of the attributes 210 from the received experiment dataset 170 corresponds to the corresponding attributes 210 in at least one of the stored experiment datasets 170 of the records 175 based on the comparison. In response, the record indexer 150 may identify the highest level of attribute detail. The highest level may correspond to the attributes 210 with the most depth that are common across both the received experiment dataset 170 and the stored experiment datasets 170 in the records 175. As discussed above, the order for the level of attribute detail from descending to ascending may be source entity, subject 130, biological sample 135, aliquot 140, and the experiment dataset 170 itself. In the example depicted in FIG. 0.3, the record indexer 150 may identify the biological sample 135' ("Tumor Sample") as the highest common level of attribute among the three experiment datasets 170, 170', and 170". The record indexer 150 may identify the aliquot 140' ("Second Aliquot") as the highest common level of attribute between the second experiment dataset 170' and the third experiment dataset 170".

When the highest common level of attribute is the experiment dataset 170, the record indexer 150 may determine that the newly received experiment dataset 170 is a duplicate. In response to the determination as a duplicate, the record indexer 150 may prevent or restrict generation of a new system identifier 180 for the newly received experiment dataset 170. Furthermore, the record indexer 150 may prevent or restrict generation of a new record 175 for the received experiment dataset 170. In some embodiments, the record indexer 150 may return a message to the data acquirer 110 that the submitted experiment dataset 170 is a duplicate. On the other hand, when the highest common level of attribute is lower than the experiment dataset 170, the record indexer 150 may determine that the received experiment dataset 170 is not a duplicate and new. The record indexer 150 may continue processing and generate a new system identifier 180 for the newly received experiment dataset 170.

In accordance with the highest level of the attribute (lower than the experiment dataset 170), the record indexer 150 may assign or determine one or more of the segments 205 to include the system identifier 180 for the newly received experiment dataset 170. For attributes 210 that are at or lower than the highest common level of attribute, the record indexer 150 may use the same corresponding segments 205. The record indexer 150 may identify the segments 205 of the system identifier 180 for the record 175 of the stored experiment dataset 170 that correspond to attributes including and lower than the highest level of attribute. For example, when the highest level of attribute is the biological sample 135, the record indexer 150 may identify the first segment 205A for the source entity, the second segment 205B for the subject 130, and the third segment 205C for the biological sample 135. Once identified, the record indexer 150 may use the identified segments 205 to assign to the system identifier 180 for the newly received experiment dataset 170.

Conversely, for attributes 210 that are greater than the highest common level of attribute, the record indexer 150 may determine or generate new segments 205 for the system identifier 180. The new segments 205 for the new system identifier 180 may differ from any of the segments 205 in other system identifiers 180 for records 175 of the experiment datasets 170 stored and maintained on the database 120. The new segments 205 may be generated using one of the counters 165 as discussed below. As such, when there is any correspondence, the system identifier 180 for the record 175 of the newly received experiment dataset 170 may at least a portion of the system identifier 180 for the record 175 of the stored experiment dataset 170 on the database 120.

In some embodiments, the record indexer 150 may maintain the set of counters 165 for the corresponding set of attributes 210 (e.g., the source entity, the subject 130, the biological sample 135, the aliquot 140, and the experiment). Each counter 165 may keep track a number of different attributes 210 across the system identifiers 180 in the database 120, and may be used to generate one or more of the segments 205 of the system identifier 180. In some embodiments, the record indexer 150 may maintain sets of counters 165 for a higher level attribute for a single value of a lower level attribute maintained using at least one counter 165. For example, a first counter 165A may keep track of a number of different source entities. A set of counters 165B may keep track of a number of different subjects 130 for each source entity. Another set of counters 165C may keep track of a number of different biological samples 135 for each subject 130 and each source entity. Another set of counters 165D may keep track of a number of different aliquots 140 for each biological sample 135, for each subject 130, and each source entity. Another set of counters 165D may keep track of a number of different experiment datasets 170 for each aliquot 140, for each biological sample 135, for each subject 130, and for each source entity. By using counters 165, the record indexer 150 may circumvent or negate the issue with colliding or overlapping segments 205 or system identifiers 180 to reference records 175 in the record database 120.

Using the counters 165, the record indexer 150 may determine or generate one or more of the segments 205 of the system identifier 180. The record indexer 150 may identify one or more counters 165 with which to use to determine the segments 205 of the system identifier 180. The identification may be based on the attributes 210 from the received experiment dataset 170 determined to correspond to the respective attributes 210 in at least one of the stored experiment datasets 170 of the records 175. In some embodiments, the record indexer 150 may identify the counters 165 that are for attributes 210 that are greater than the highest common level of attribute. The record indexer 150 may identify the counter 165 for the attribute 210 one level greater than the highest common level. For example, when the highest common level of attribute is identified as biological sample 135, the record indexer 150 may identify the counter 165 for the aliquot 140 of the same biological sample 135, the same subject 130, and source entity.

When there is a counter 165 identified, the record indexer 150 may update (e.g., increment) the value of the counter 165. The record indexer 150 may set the corresponding segment 205 of the new system identifier 180 to the updated value of the counter 165. Conversely, when there is no counter 165 identified for the next level of attribute 210, the record indexer 150 may create or initialize a new counter 165 for the attribute 210. The new counter 165 may be initially set to a predefined value (e.g., null or a random number). The record indexer 150 may set the corresponding segment 205 of the new system identifier 180 to the value of the counter 165. For each of the higher levels of attributes 210, the record indexer 150 may create or initialize a new counter 165 for the attribute 210 that is initially set to a predefined value. The record indexer 150 may set the remaining segments 205 of the new system identifier 180 using the new value of the counters 165.

Upon generating the system identifier 180, the record indexer 150 may instantiate, create, or generate the record 175 to identify, insert, or include the experiment dataset 170. Once generated, the record indexer 150 may insert or include the experiment dataset 170 into the record 175. In some embodiments, the record indexer 150 may insert or include the associated metadata into the record 175. The record indexer 150 may also associate the system identifier 180 with the record 175. Once generated, the record indexer 150 may store and maintain the record 175 onto the record database 120. In some embodiments, the record indexer 150 may store and maintain the association between the record 175 and the system identifier 180 on the record database 120.

In conjunction, the client device 115 may send, provide, or transmit at least one query 190 for records via the network 125 to the records management service 105. The query 190 may be a request for records 175 that correspond to or satisfy the specified search constraints. The constraints may identify, define, or otherwise include values for attributes 210 of experiment datasets 170. The constraints may also define Boolean conditions for the values of attributes 210. For instance, the query 190 may be for records 175 with experiment datasets 170 for a particular aliquot 140 from samples 135 labeled as tumorous. In some embodiments, the query 190 may include one or more segments 205 of the system identifiers 180 corresponding to the records 175 to be retrieved. In some embodiments, an application running on the client device 115 may generate the query 190. For example, a web application may provide a user interface for entering values for the attributes 210 of experiment datasets 170 in records 175 maintained on the record database 120. Upon generation, the client device 115 may send the query 190 to the records management service 105.

The query handler 155 executing on the records management service 105 may retrieve, identify, receive at least one query 190 for records from the client device 115. With receipt, the query handler 155 may parse the query 190 to identify the one or more values for attributes 210 of experiment datasets 170 to be retrieved. Using the values for attributes 210 defined by the query 190, the query handler 155 may search the records 175 of the record database 120. The query handler 155 may identify the experiment datasets 170 of the records 175 on the record database 120 that correspond to the values defined by the query 190. In some embodiments, the query handler 155 may apply the Boolean condition specified by the query 190 in identifying the experiment datasets 170. In some embodiments, the query handler 155 may identify a set number of experiment datasets 170 with attributes 210 that match the values specified by the query 190.

The output generator 160 executing on the records management service 105 may generate at least one output 195 to provide to the client device 115. The output 195 may include the records 175 with experiment datasets 170 having attributes 210 that satisfy the constraints of the query 190. In some embodiments, the output 195 may include or be a script for visualization of the results. For example, the script may be in accordance with Hypertext Markup Language (HTML5), and may include objects to render the results. Upon generation, the output generator 160 may provide, send, or transmit the output 195 to the client device 115 via the network 125. With receipt, the client device 115 may display or present the output 195. In some embodiments, the client device 115 may execute the script to present the visualization of the query result. The details of the visualization are explained herein below in conjunction with FIGS. 5-7C.

Figure 5:
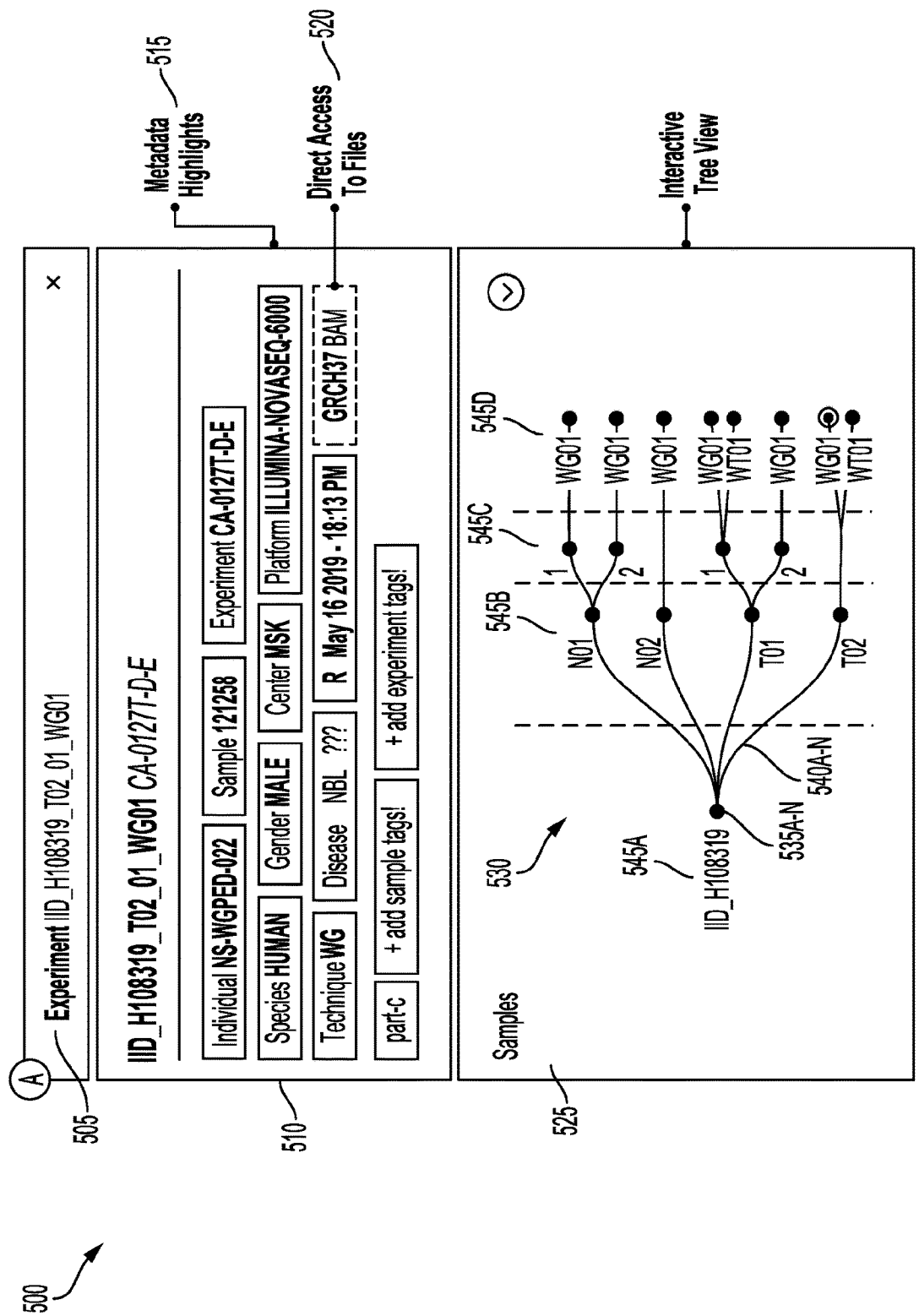
FIG. 5 is an illustration of an example user interface including a graph element generated using the system for maintaining and accessing experiment data in accordance with an illustrative embodiment.

Referring now to FIG. 5, depicted is an illustration of an example user interface 500 generated using the system for maintaining and accessing experiment data. The user interface 500 may be generated by the output generator 160 to present the records 175 found using the query 190. The user interface 500 may include at least one element 505 (sometimes herein referred to as a card) to indicate or present the system identifier 180 (e.g., "IID_H108310_T02_01_WG01"). The user interface 500 may include at least one element 510 (also sometimes herein referred to as a card) to indicate or present a list of tags. The list of tags may include metadata highlights 515 associated with the experiment dataset 170 corresponding to the system identifier 180. In addition, the list of tags may include a link 520 to access a file associated with the experiment dataset 170 corresponding to the system identifier 180.

The user interface 500 may include at least one element 525 (sometimes herein referred to as a card) to present a graph element 530. The graph element 530 may be generated using the records 175 or the system identifiers 180 for the records 175 maintained and stored on the record database 120. The graph element 530 may be used to indicate relationships or associations among the experiment datasets 170, records 175, or the system identifiers 180. The graph element 530 may include a set of nodes 535A-N (hereinafter generally referred to as nodes 535) and a set of edges 540A-N (hereinafter generally referred to as edges 540) to connect the nodes 535. The nodes 535 and edges 540 may be arranged over a set of levels 545A-D (hereinafter generally referred to as levels 545). Each level 545 may correspond to one of the attributes 210 (e.g., source entity, subject 130, biological sample 135, aliquot 140, and the experiment dataset 170). Each node 535 may represent or correspond to an attribute 210 of an experiment dataset 170 at the respective level 545. The edges 540 may represent or correspond to associations among the attributes 210 of the experiment datasets 170 between two or more of the levels 545.

In the example of the graph element 530 depicted, the first level 545A may include one node 535 that corresponds or represents the subject 130 common to the records 175 as indicated in the second segment 205B ("IID_H108310") of the system identifiers 180. The second level 545B may include a set of nodes 535. Each node 535 of the second level 545B may correspond to or represent a respective biological sample 135 (e.g., "N01," "N02," "T01," and "T02") as indicated by the third segment 205C of the system identifiers 180. The association between the nodes 535 of the second level 545B and the node 535 of the first level 545A may be indicated or represented using a set of edges 540. The set of edges 540 between the first level 545A and the second level 545B may indicate that all the biological samples 135 are obtained from the common subject 130.

Continuing on in the graph element 530, the third level 545C may include a set of nodes 535. Each node 535 of the third level 545C may correspond to or represent a respective aliquot 140 (e.g., "1" or "2") as indicated by the fourth segment 205D of the system identifiers 180. The associations between the nodes 535 of the third level 545C and the nodes 535 of the second level 545B may be indicated or represented using a set of edges 540. The set of edges 540 between the second level 545B and the third level 545C may indicate that the aliquots 140 are obtained from the respective biological samples 135 of the common subject 130. The fourth level 545D may include a set of nodes 535. Each node 535 of the fourth level 545D may correspond to or represent a respective experiment dataset 170 (e.g., "WG01" and "WT01") as indicated by the fifth segment 205E of the system identifiers 180. The associations between the nodes 535 of the fourth level 545D and the nodes 535 of the third level 545C may be indicated or represented using a set of edges 540. The set of edges 540 between the third level 545C and the fourth level 545D may indicate that the experiment dataset 170 was acquired using the respective aliquot 140.

To generate the graph element 530, the output generator 160 may identify attributes 210 from each of the system identifiers 180 for the experiment datasets 170 of the records 175. In some embodiments, the experiment datasets 170 may be found from the record database 120 using the constraints defined in the query 190 for records. The attributes 210 may include, for example, the source entity, the subject 130, the biological sample 135, the aliquot 140, and the experiment dataset 170 itself. For each attribute 210, the output generator 160 may determine or identify one or more different values across the system identifiers 180. The output generator 160 may generate the nodes 535 based on the corresponding values of the attributes 210 identified from the system identifiers 180. In addition, the output generator 160 may determine or identify associations among the attributes 210 of the system identifiers 180. In some embodiments, the output generator 160 may identify the associations between attributes 210 of two consecutive levels of details (e.g., the subject 130 and biological samples 135). The two consecutive levels of attribute details may correspond to consecutives levels 545 in the graph element 530. Based on the identified associations, the output generator 160 may generate the edges 540 to indicate the associations among the nodes 535. Upon generation, the output generator 160 may provide the graph element 530 to the client device 115 for presentation.

Figure 6:
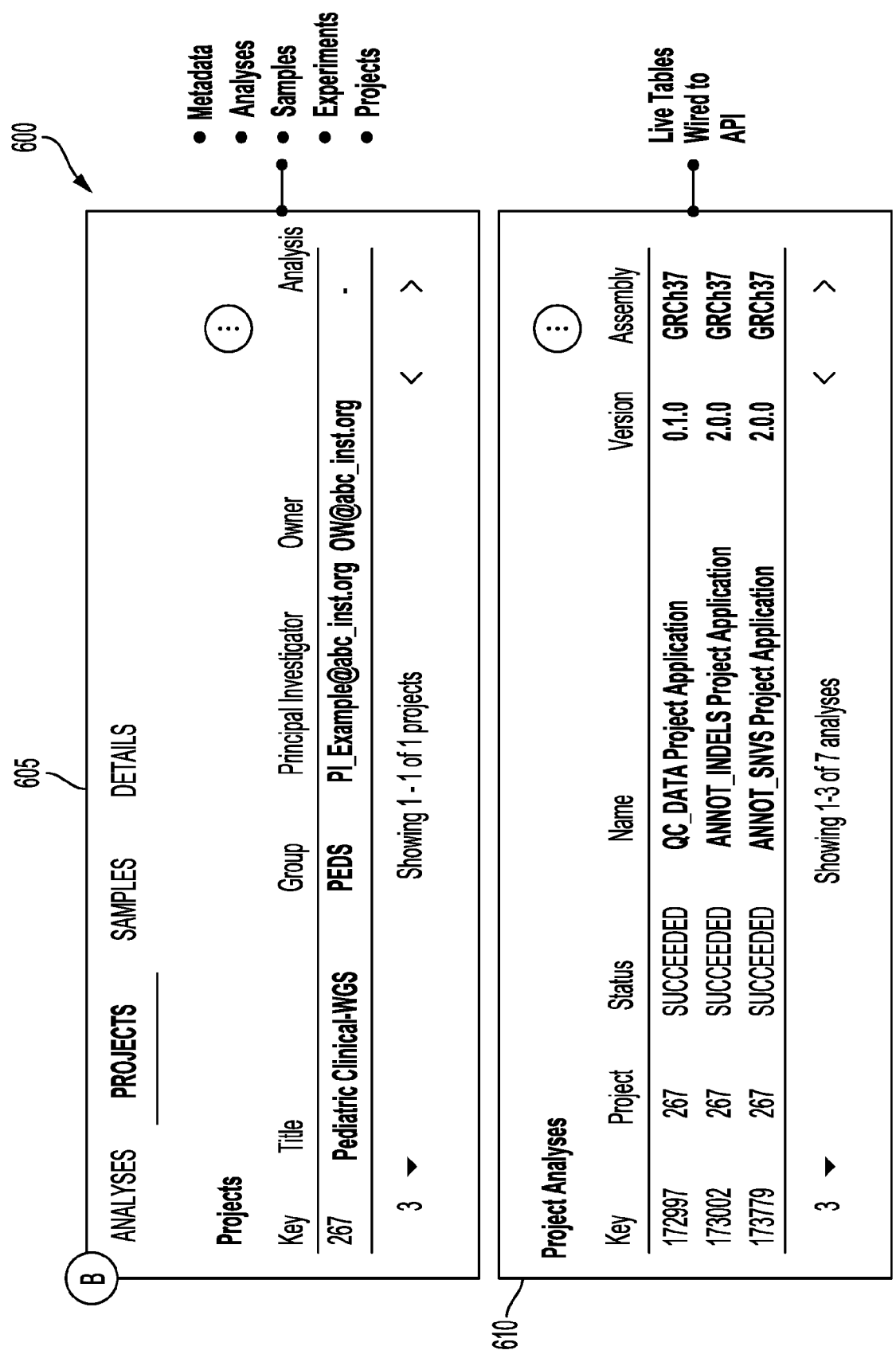
FIG. 6 is an illustration of an example user interface including elements for related data to the graph element generated using the system for maintaining and accessing experiment data in accordance with an illustrative embodiment.

Referring now to FIG. 6, depicted is an illustration of an example user interface 600 including elements for related data generated using the system for maintaining and accessing experiment data. The user interface 600 may be generated by the output generator 160 to present the records 175 found using the query 190. The user interface 600 may include at least one element 605 (sometimes herein referred to as a card). The element 605 may indicate or present various types of information associated with the experiment datasets 170, such as metadata, analyses, samples, experiment types, and projects, among others. In the example depicted, the element 605 may include the investigator associated with one or more of the experiment datasets 170. The user interface 600 may include at least one element 610 (sometimes herein referred to as a card). The element 610 may indicate or present various types of information associated with the projects under which experiments were carried out. The element 610 may include one or more links to analyses (e.g., in the form of tables) associated with the experiment datasets 170.

Figure 7B:
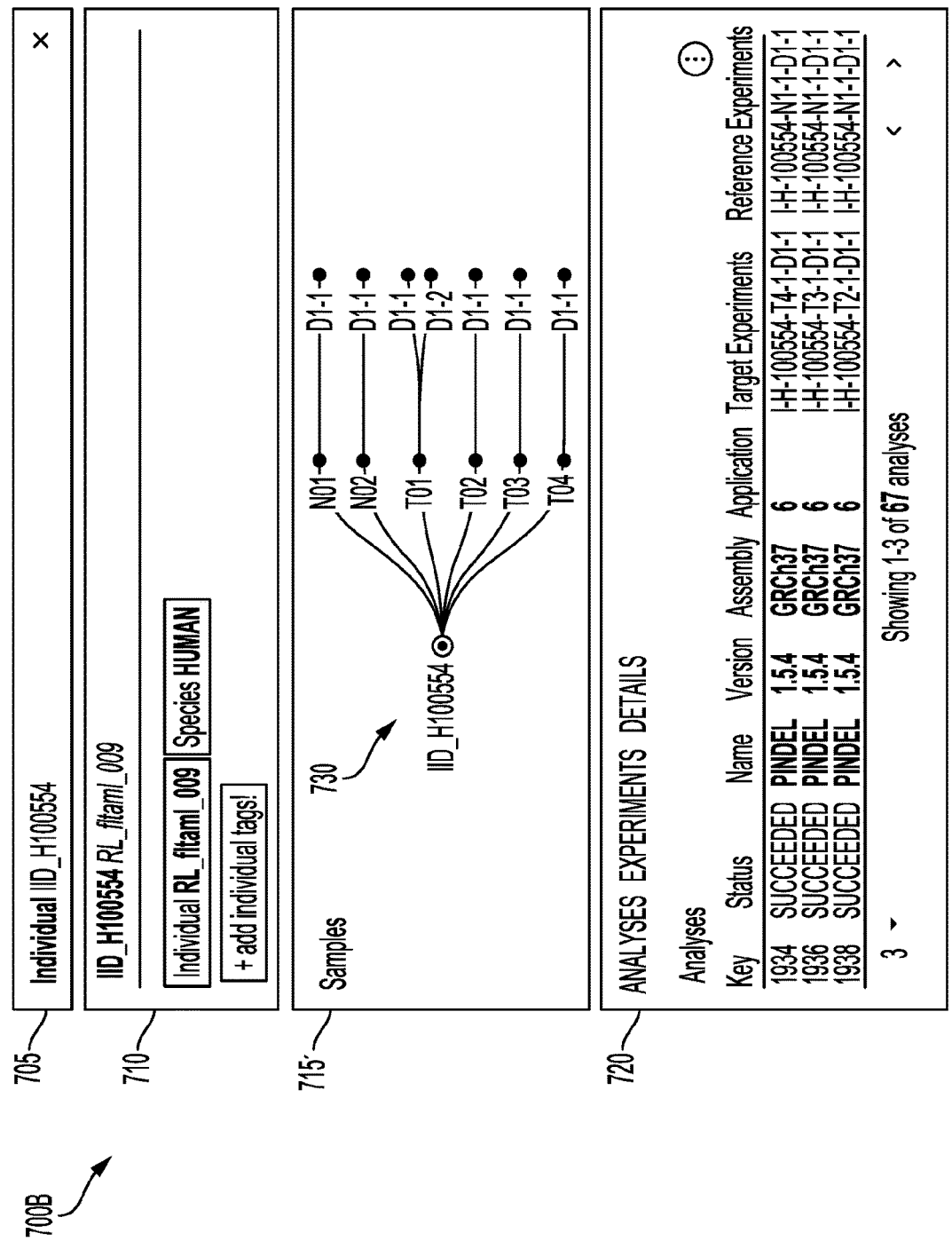
Figure 7C:
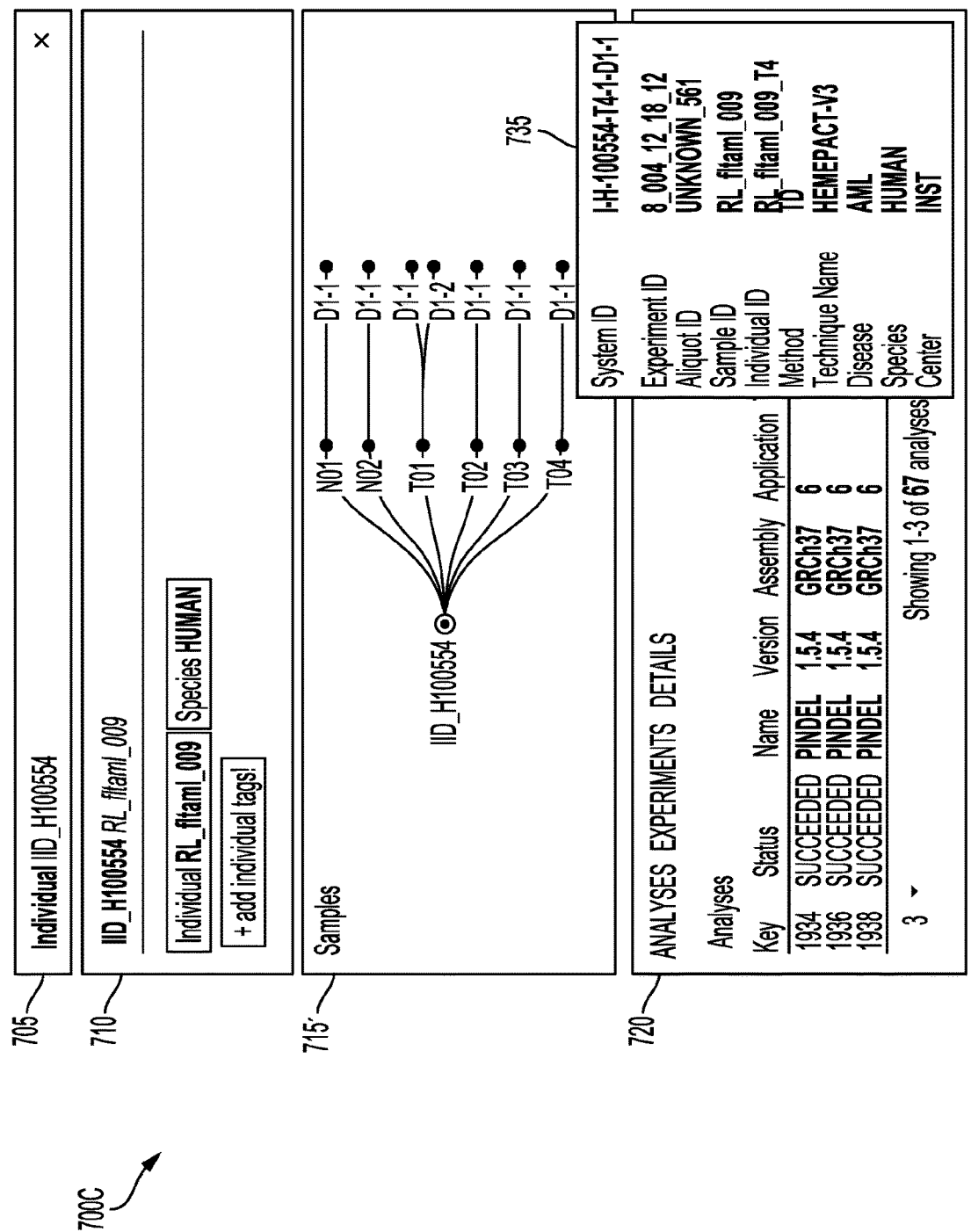

Referring now to FIGS. 7A-7C, depicted are illustrations of example user interfaces 700A-C in response to user interactions as configured by the system for maintaining and accessing experiment data. The user interfaces 700A-C may be generated by the output generator 160 to present the records 175 found using the query 190. The user interface 700A may include an element 705 to present the second segment 205B of the system identifier 180 for one or more records 175 to indicate the subject 130 (or "individual"). The user interface 700A may include an element 710 to present metadata associated with the experiment datasets 170 of the records 175 in relation to the subject 130 that is indicated in the element 705. The user interface 700A may include an element 715 to present a graph element 530 of the samples with one node 535 corresponding to the subject 130. The user interface 700A may include an element 720 to present a list of analyses associated with the experiment datasets 170. The experiment datasets 170 may be acquired from the aliquots 140 of the biological samples 135 of the subject 130 indicated in the element 705. The user interface 700A may also include an element 725 to present project information in connection with the experiment datasets 170. The project information may include a title, a research group, a principal investigator, owner, and coordinator, among others.

The output generator 160 may monitor for interactions with one or more elements (e.g., nodes 535 or edges 540 of the graph element 530) of the user interface (e.g., the user interface 700A). In some embodiments, the script provided by the output generator 160 may provide interactivity through the one or more elements of the user interface. In response to detecting an interaction on an element, the output generator 160 (or the script) may provide a user element to present information associated with the element. In some embodiments, the output generator 160 may transition or change the user interface in response to the interaction.

Upon detecting an interaction 730 with the node in the graph element presented in the interface 715, the user interface 700A may transition to the user interface 700B. The user interface 700B may include the same elements 705, 710, 720, and 725. In the user interface 700B, the element 715 may be expanded to element 715' to present a graph element 730. The graph element 730 may have nodes 535 and edges 540 arranged over levels 545 for the experiment datasets 170 associated with the subject 130 as identified in the subject 130. In response to detecting another interaction on one of the nodes 535 of the graph element, the user interface 700B may transition to the user interface 700C. The user interface 700C may include an element 735 to present various types of information associated with the node 535 (and by extension, the experiment dataset 170 represented by the node 535) upon which the interaction is detected. The user element 735 may include, for example as depicted, the system identifier 180, experiment identifier, aliquot identifier, sample identifier, individual identifier, method, technique name, disease, species, and center, among others.

Figure 8:
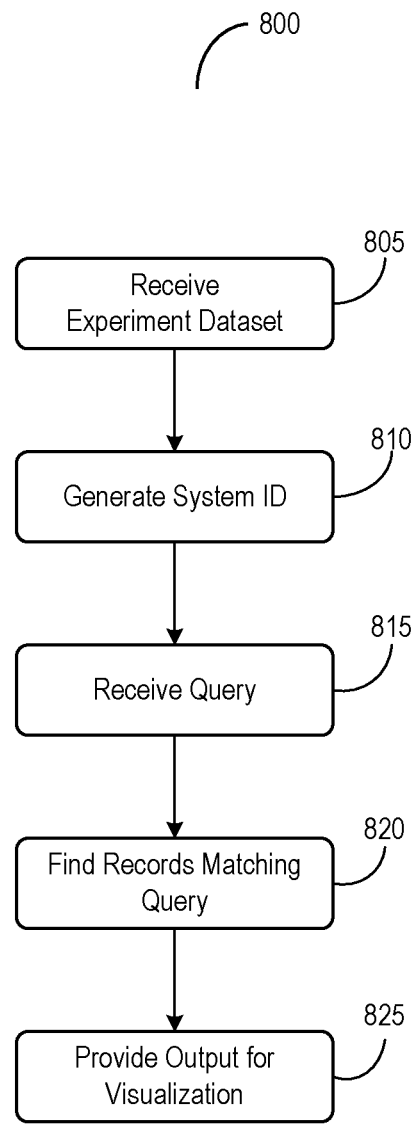
FIG. 8 is a flow diagram of a method of maintaining and accessing experiment data in accordance with an illustrative embodiment.

Referring now to FIG. 8, depicted is a flow diagram of a method 800 of maintaining and accessing experiment data. The method 800 may be implemented or performed using any component described herein, such as those detailed herein in conjunction with system 100 (e.g., the records management system 105, the data acquirer 110, and the client device 115) and the server system 900 detailed herein in Section B. In brief overview, a data processing system may receive an experiment dataset (805). The data processing system may generate a system identifier (810). The data processing system may receive a query (815). The data processing system may find records matching the query (820). The data processing system may provide a visualization (825).

In further detail, a data processing system (e.g., the record management service 105) may receive an experiment dataset (e.g., the experiment dataset 170) (805). The experiment dataset may have been generated from performing an one evaluation on at least one aliquot (e.g., the aliquot 140) that is obtained from an biological sample (e.g., the biological sample 135) of a subject (e.g., the subject 130). The experiment dataset may be associated with metadata. The experiment dataset may be received from a data acquirer (e.g., the data acquirer 110).

The data processing system may generate a system identifier (e.g., the system identifier 180) (810). The system identifier may reference a record (e.g., the record 175) including the experiment dataset to be stored and maintained on a database (e.g., the record database 120). The data processing system may generate the system identifier based on attributes (e.g., the attributes 210) associated with the experiment dataset. The system identifier may include a set of segments (e.g., segments 205). Each segment may correspond or reference one of the attributes. Upon generation, the data processing system may store the record referenced by the system identifier.

The data processing system may receive a query (e.g., the query 190) (815). The query received from a client device (e.g., the client device 115) may include one or more constraints defining attributes of experiment datasets to be retrieved. The data processing system may find records (e.g., the records 175) matching the query (820). Using the attributes specified by the query, the data processing system may search for matching records. The data processing system may provide an output (e.g., the output 195) for visualization (825). The output may include the records that satisfy the query. The output may also include a script to present a user interface (e.g., the user interface 500, 600, or 700A-C). The user interface may include various types of information associated with the experiment datasets.

B. Computing and Network Environment

Figure 9:
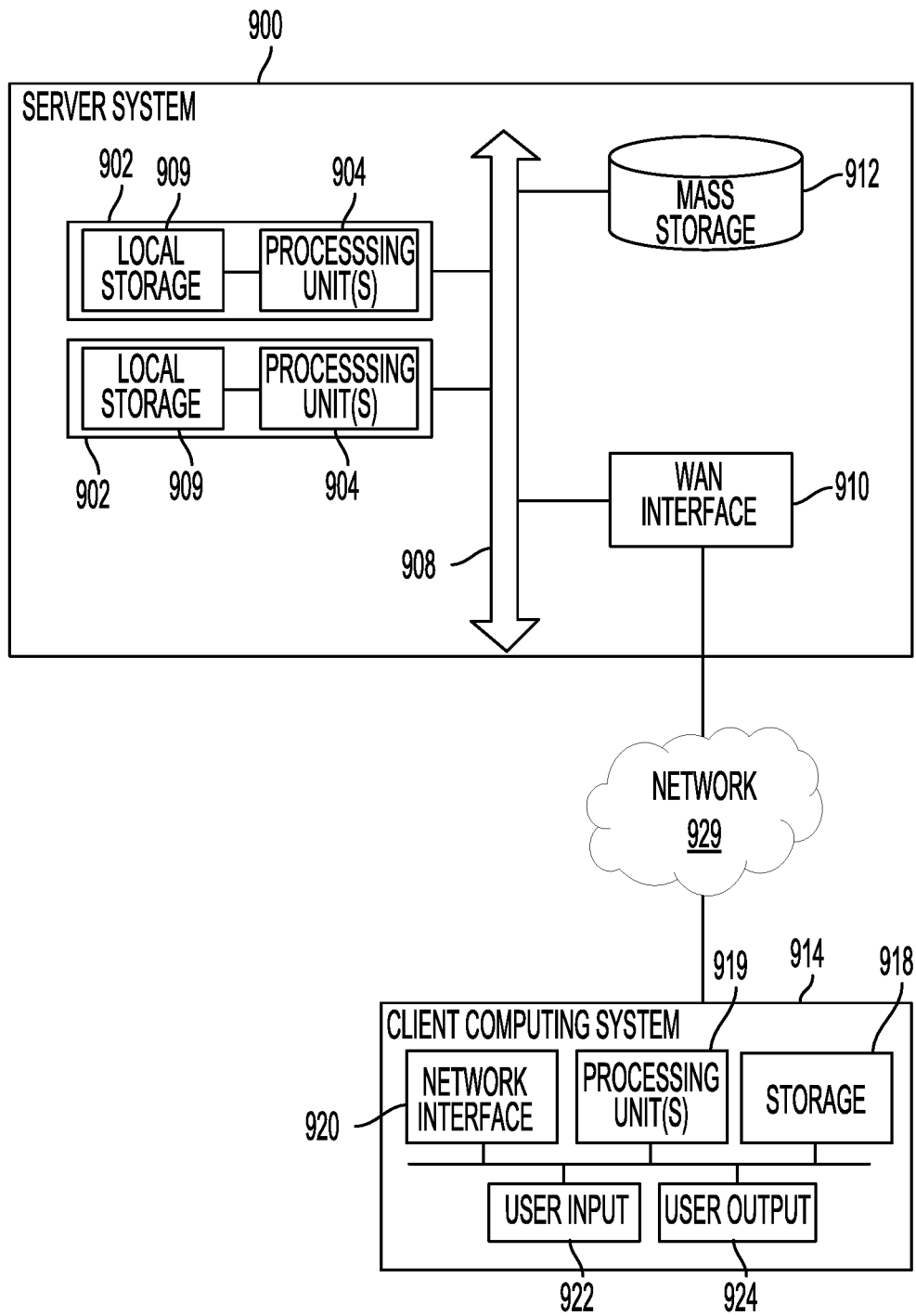
FIG. 9 is a block diagram of a server system and a client computer system in accordance with an illustrative embodiment.

Various operations described herein can be implemented on computer systems. FIG. 9 shows a simplified block diagram of a representative server system 900, client computer system 914, and network 926 usable to implement certain embodiments of the present disclosure. In various embodiments, server system 900 or similar systems can implement services or servers described herein or portions thereof. Client computer system 914 or similar systems can implement clients described herein. The system 100 described herein can be similar to the server system 900. Server system 900 can have a modular design that incorporates a number of modules 902 (e.g., blades in a blade server embodiment); while two modules 902 are shown, any number can be provided. Each module 9s02 can include processing unit(s) 904 and local storage 906.

Processing unit(s) 904 can include a single processor, which can have one or more cores, or multiple processors. In some embodiments, processing unit(s) 904 can include a general-purpose primary processor as well as one or more special-purpose co-processors such as graphics processors, digital signal processors, or the like. In some embodiments, some or all processing units 904 can be implemented using customized circuits, such as application specific integrated circuits (ASICs) or field programmable gate arrays (FPGAs). In some embodiments, such integrated circuits execute instructions that are stored on the circuit itself. In other embodiments, processing unit(s) 904 can execute instructions stored in local storage 906. Any type of processors in any combination can be included in processing unit(s) 904.

Local storage 906 can include volatile storage media (e.g., DRAM, SRAM, SDRAM, or the like) and/or non-volatile storage media (e.g., magnetic or optical disk, flash memory, or the like). Storage media incorporated in local storage 906 can be fixed, removable or upgradeable as desired. Local storage 906 can be physically or logically divided into various subunits such as a system memory, a read-only memory (ROM), and a permanent storage device. The system memory can be a read-and-write memory device or a volatile read-and-write memory, such as dynamic random-access memory. The system memory can store some or all of the instructions and data that processing unit(s) 904 need at runtime. The ROM can store static data and instructions that are needed by processing unit(s) 904. The permanent storage device can be a non-volatile read-and-write memory device that can store instructions and data even when module 902 is powered down. The term "storage medium" as used herein includes any medium in which data can be stored indefinitely (subject to overwriting, electrical disturbance, power loss, or the like) and does not include carrier waves and transitory electronic signals propagating wirelessly or over wired connections.

In some embodiments, local storage 906 can store one or more software programs to be executed by processing unit(s) 904, such as an operating system and/or programs implementing various server functions such as functions of the system 100 of FIG. 1 or any other system described herein, or any other server(s) associated with system 100 or any other system described herein.

"Software" refers generally to sequences of instructions that, when executed by processing unit(s) 904 cause server system 900 (or portions thereof) to perform various operations, thus defining one or more specific machine embodiments that execute and perform the operations of the software programs. The instructions can be stored as firmware residing in read-only memory and/or program code stored in non-volatile storage media that can be read into volatile working memory for execution by processing unit(s) 904. Software can be implemented as a single program or a collection of separate programs or program modules that interact as desired. From local storage 906 (or non-local storage described below), processing unit(s) 904 can retrieve program instructions to execute and data to process in order to execute various operations described above.

In some server systems 900, multiple modules 902 can be interconnected via a bus or other interconnect 908, forming a local area network that supports communication between modules 902 and other components of server system 900. Interconnect 908 can be implemented using various technologies including server racks, hubs, routers, etc.

A wide area network (WAN) interface 910 can provide data communication capability between the local area network (interconnect 908) and the network 926, such as the Internet. Technologies can be used, including wired (e.g., Ethernet, IEEE 802.3 standards) and/or wireless technologies (e.g., Wi-Fi, IEEE 802.11 standards).

In some embodiments, local storage 906 is intended to provide working memory for processing unit(s) 904, providing fast access to programs and/or data to be processed while reducing traffic on interconnect 908. Storage for larger quantities of data can be provided on the local area network by one or more mass storage subsystems 912 that can be connected to interconnect 908. Mass storage subsystem 912 can be based on magnetic, optical, semiconductor, or other data storage media. Direct attached storage, storage area networks, network-attached storage, and the like can be used. Any data stores or other collections of data described herein as being produced, consumed, or maintained by a service or server can be stored in mass storage subsystem 912. In some embodiments, additional data storage resources may be accessible via WAN interface 910 (potentially with increased latency).

Server system 900 can operate in response to requests received via WAN interface 910. For example, one of modules 902 can implement a supervisory function and assign discrete tasks to other modules 902 in response to received requests. Work allocation techniques can be used. As requests are processed, results can be returned to the requester via WAN interface 910. Such operation can generally be automated. Further, in some embodiments, WAN interface 910 can connect multiple server systems 900 to each other, providing scalable systems capable of managing high volumes of activity. Other techniques for managing server systems and server farms (collections of server systems that cooperate) can be used, including dynamic resource allocation and reallocation.

Server system 900 can interact with various user-owned or user-operated devices via a wide-area network such as the Internet. An example of a user-operated device is shown in FIG. 9 as client computing system 914. Client computing system 914 can be implemented, for example, as a consumer device such as a smartphone, other mobile phone, tablet computer, wearable computing device (e.g., smart watch, eyeglasses), desktop computer, laptop computer, and so on.

For example, client computing system 914 can communicate via WAN interface 910. Client computing system 914 can include computer components such as processing unit(s) 916, storage device 918, network interface 920, user input device 922, and user output device 924. Client computing system 914 can be a computing device implemented in a variety of form factors, such as a desktop computer, laptop computer, tablet computer, smartphone, other mobile computing device, wearable computing device, or the like.

Processor 916 and storage device 918 can be similar to processing unit(s) 904 and local storage 906 described above. Suitable devices can be selected based on the demands to be placed on client computing system 914; for example, client computing system 914 can be implemented as a "thin" client with limited processing capability or as a high-powered computing device. Client computing system 914 can be provisioned with program code executable by processing unit(s) 916 to enable various interactions with server system 900.

Network interface 920 can provide a connection to the network 926, such as a wide area network (e.g., the Internet) to which WAN interface 910 of server system 900 is also connected. In various embodiments, network interface 920 can include a wired interface (e.g., Ethernet) and/or a wireless interface implementing various RF data communication standards such as Wi-Fi, Bluetooth, or cellular data network standards (e.g., 3G, 4G, LTE, etc.).

User input device 922 can include any device (or devices) via which a user can provide signals to client computing system 914; client computing system 914 can interpret the signals as indicative of particular user requests or information. In various embodiments, user input device 922 can include any or all of a keyboard, touch pad, touch screen, mouse or other pointing device, scroll wheel, click wheel, dial, button, switch, keypad, microphone, and so on.

User output device 924 can include any device via which client computing system 914 can provide information to a user. For example, user output device 924 can include a display to display images generated by or delivered to client computing system 914. The display can incorporate various image generation technologies, e.g., a liquid crystal display (LCD), light-emitting diode (LED) including organic light-emitting diodes (OLED), projection system, cathode ray tube (CRT), or the like, together with supporting electronics (e.g., digital-to-analog or analog-to-digital converters, signal processors, or the like). Some embodiments can include a device such as a touchscreen that functions as both input and output device. In some embodiments, other user output devices 924 can be provided in addition to or instead of a display. Examples include indicator lights, speakers, tactile "display" devices, printers, and so on.

Some embodiments include electronic components, such as microprocessors, storage and memory that store computer program instructions in a computer readable storage medium. Many of the features described in this specification can be implemented as processes that are specified as a set of program instructions encoded on a computer readable storage medium. When these program instructions are executed by one or more processing units, they cause the processing unit(s) to perform various operations indicated in the program instructions. Examples of program instructions or computer code include machine code, such as is produced by a compiler, and files including higher-level code that are executed by a computer, an electronic component, or a microprocessor using an interpreter. Through suitable programming, processing unit(s) 904 and 916 can provide various functionality for server system 900 and client computing system 914, including any of the functionality described herein as being performed by a server or client, or other functionality.

It will be appreciated that server system 900 and client computing system 914 are illustrative and that variations and modifications are possible. Computer systems used in connection with embodiments of the present disclosure can have other capabilities not specifically described here. Further, while server system 900 and client computing system 914 are described with reference to particular blocks, it is to be understood that these blocks are defined for convenience of description and are not intended to imply a particular physical arrangement of component parts. For instance, different blocks can be but need not be located in the same facility, in the same server rack, or on the same motherboard.

Further, the blocks need not correspond to physically distinct components. Blocks can be configured to perform various operations, e.g., by programming a processor or providing appropriate control circuitry, and various blocks might or might not be reconfigurable depending on how the initial configuration is obtained. Embodiments of the present disclosure can be realized in a variety of apparatus including electronic devices implemented using any combination of circuitry and software.

While the disclosure has been described with respect to specific embodiments, one skilled in the art will recognize that numerous modifications are possible. Embodiments of the disclosure can be realized using a variety of computer systems and communication technologies including but not limited to specific examples described herein. Embodiments of the present disclosure can be realized using any combination of dedicated components and/or programmable processors and/or other programmable devices. The various processes described herein can be implemented on the same processor or different processors in any combination. Where components are described as being configured to perform certain operations, such configuration can be accomplished, e.g., by designing electronic circuits to perform the operation, by programming programmable electronic circuits (such as microprocessors) to perform the operation, or any combination thereof. Further, while the embodiments described above may make reference to specific hardware and software components, those skilled in the art will appreciate that different combinations of hardware and/or software components may also be used and that particular operations described as being implemented in hardware might also be implemented in software or vice versa.

Computer programs incorporating various features of the present disclosure may be encoded and stored on various computer readable storage media; suitable media include magnetic disk or tape, optical storage media such as compact disk (CD) or DVD (digital versatile disk), flash memory, and other non-transitory media. Computer readable media encoded with the program code may be packaged with a compatible electronic device, or the program code may be provided separately from electronic devices (e.g., via Internet download or as a separately packaged computer-readable storage medium).

Thus, although the disclosure has been described with respect to specific embodiments, it will be appreciated that the disclosure is intended to cover all modifications and equivalents within the scope of the following claims.

What is claimed is:

1. A system for maintaining experiment data, comprising:
 a data processing system having one or more processors coupled with memory, the data processing system configured to maintain a database in accordance with a plurality of system identifiers, each system identifier of the plurality of system identifiers having a plurality of segments for a corresponding plurality of attributes, each of the plurality of segments in each system identifier comprising:
  a first segment to reference an instance corresponding to a source entity;
  a second segment, with the first segment, to reference a subject;
  a third segment, with the first segment and the second segment, to reference a biological sample acquired from the subject;

a fourth segment, with the first segment, the second segment, and the third segment, to reference a aliquot corresponding to at least a portion of the biological sample; and a fifth segment, with the first segment, the second segment, the third segment, and the fourth segment, to reference a dataset of an experiment performed on the aliquot of at least the portion of the biological sample that is acquired from the subject.

2. The system of claim 1, wherein the data processing system is further configured to:

receive, from a data acquirer associated with the source entity, the dataset of the experiment performed on the aliquot obtained from at least the portion of the biological sample of the subject;

determine, responsive to receipt of the dataset of the experiment and subsequent to generation of a first system identifier having a first attribute, that a second attribute including at least one of the source entity, the subject, the biological sample, or the aliquot upon which the experiment is performed corresponds to the first attribute of the first system identifier; and generate, responsive to the determination, a second system identifier for a record including the dataset of the experiment based on the first system identifier, at least a portion of the second system identifier matching a corresponding portion of the first system identifier.

3. The system of claim 1, wherein the data processing system is further configured to:

determine that a first attribute of a first system identifier including at least one of the source entity, the subject, the biological sample, or the aliquot corresponds to a second attribute of the dataset of the experiment for a second system identifier;

identify, from the plurality of segments of the first system identifier, one or more segments corresponding to the first attribute determined to correspond to the second attribute; and assign the one or more segments of the first system identifier to corresponding one or more segments of the second system identifier to associate the first system identifier with the second system identifier.

4. The system of claim 1, wherein the data processing system is further configured to:

maintain a plurality of counters for the corresponding plurality of attributes, the plurality of attributes including the source entity, the subject, the biological sample, and the aliquot;

determine, responsive to receipt of the dataset of the experiment, that a first attribute of a first system identifier including at least one of the source entity, the subject, the biological sample, or the aliquot corresponds to a second attribute of the dataset of the experiment for a second system identifier;

identify, responsive to the determination, a counter from the plurality of counters for the first attribute determine to correspond to the second attribute; and assign, using the counter, the fifth segment of the second system identifier for the dataset of the experiment.

5. The system of claim 1, wherein the data processing system is further configured to:

determine, responsive to receipt of the dataset of the experiment, that a plurality of attributes identified by a first system identifier including at least one of the source entity, the subject, the biological sample, the aliquot, and the dataset, matches a plurality of attributes derived from the dataset; and restrict, responsive to the determination, generation of a second system identifier for the dataset using the plurality of attributes derived from the dataset of the experiment.

6. The system of claim 1, wherein the data processing system is further configured to:

receive, from a client device, a query for records identifying one or more attributes of a plurality of attributes, the plurality of attributes including the source entity, the subject, the biological sample, the aliquot, and the experiment; and provide, from a plurality of records maintained on the database, a subset of records corresponding to the one or more attributes as identified in the query for records to the client device.

7. The system of claim 1, wherein the data processing system is further configured to provide a graph element using at least one of the plurality of system identifiers, the graph element including a plurality of nodes and a plurality of edges to connect the plurality of nodes, the plurality of nodes corresponding to a plurality of attributes, the plurality of edges corresponding to associations among the plurality of attributes.

8. The system of claim 1, wherein at least one of the plurality of segments in each system identifier further comprises a marker of a plurality of markers and a unique value, the plurality of markers indicating a condition for a corresponding attribute.

9. A system for accessing experiment data, comprising:

a data processing system having one or more processors coupled with memory, the data processing system configured to:

generate, using a plurality of system identifiers for a corresponding plurality of records that are maintained on a database, a graph element comprising:

a first level having a first node, the first node corresponding to a subject common to the plurality of records as indicated by a first segment of each of the plurality of system identifiers;

a second level having a second set of nodes, each of the second set of nodes corresponding to a aliquot for at least one record of the plurality of records as indicated by the first segment and a second segment of at least one corresponding system identifier of the plurality of system identifiers;

a first set of edges between each of the second set of nodes of the second level to the first node of the first level, each edge of the first set of edges indicating that the aliquot is obtained from the subject;

a third level having a third set of nodes, each of the third set of nodes corresponding to an experiment performed on the aliquot of a corresponding record of the plurality of records as indicated by the first segment, the second segment, and a third segment of a corresponding system identifier of the plurality of system identifiers; and a second set of edges between each of the third set of nodes of the third level and a corresponding node in the second set of nodes of the second level, each edge of the second set of edges indicating that the experiment is performed on the corresponding aliquot; and provide the graph element on a user interface for presentation.

10. The system of claim 9, wherein the data processing system is further configured to:

identify, from each of the plurality of system identifiers, a plurality of attributes including the subject, the aliquot, and the dataset of the experiment; and generate, based on the plurality of attributes, the first node of the first level, the second set of nodes of the second level, and the third set of nodes of the third level.

11. The system of claim 9, wherein the data processing system is further configured to:

identify, from among the plurality of records, a first set of associations between aliquots for at least a first subset of the plurality of records and the subject;

identify, from among the plurality of records, a second set of associations between datasets of the experiment for at least a second subset of the plurality of records and the aliquots;

generate the first set of edges based on the first set of associations; and generate the second set of edges based on the second set of associations.

12. The system of claim 9, wherein the data processing system is further configured to:

monitor, via the user interface, an interaction with a node from the first node, the second set of nodes, and the third set of nodes of the graph element; and provide, responsive to detection of the interaction with the node, a user element including information on the node.

13. The system of claim 9, wherein the data processing system is further configured to maintain the plurality of records on the database in accordance with the plurality of system identifiers, each system identifier of the plurality of system identifiers having a plurality of segments for a corresponding plurality of attributes.

14. The system of claim 9, wherein the user interface further comprises a plurality of elements corresponding to a plurality of attributes across the plurality of records used to generate the graph element.

15. A method of accessing experiment data, comprising:

maintaining, by a data processing system, a database in accordance with a plurality of system identifiers, each system identifier of the plurality of system identifiers having a plurality of segments for a corresponding plurality of attributes, each of the plurality of segments in each system identifier comprising:

a first segment to reference an instance corresponding to a source entity;

a second segment, with the first segment, to reference a subject;

a third segment, with the first segment and the second segment, to reference a biological sample acquired from the subject;

a fourth segment, with the first segment, the second segment, and the third segment, to reference a aliquot corresponding to at least a portion of the biological sample; and a fifth segment, with the first segment, the second segment, the third segment, and the fourth segment, to reference a dataset of an experiment performed on the aliquot of at least the portion of the biological sample that is acquired from the subject.

16. The method of claim 15, further comprising:

receiving, by the data processing system, from a data acquirer associated with the source entity, the dataset of the experiment performed on the aliquot obtained from at least the portion of the biological sample of the subject;

determining, by the data processing system, responsive to receiving the dataset of the experiment and subsequent to generation of a first system identifier having a first attribute, that a second attribute including at least one of the source entity, the subject, the biological sample, or the aliquot upon which the experiment is performed corresponds to the first attribute of the first system identifier; and generating, by the data processing system, responsive to determining, a second system identifier for a record including the dataset of the experiment based on the first system identifier, at least a portion of the second system identifier matching a corresponding portion of the first system identifier.

17. The method of claim 15, further comprising:

maintaining, by the data processing system, on the database, a plurality of counters for a corresponding plurality of attributes, the plurality of attributes including the source entity, the subject, the biological sample, and the aliquot;

determining, by the data processing system, responsive to receiving the dataset of the experiment, that a first attribute of a first system identifier including at least one of the source entity, the subject, the biological sample, or the aliquot corresponds to a second attribute of the dataset of the experiment for a second system identifier;

identifying, by the data processing system, responsive to determining, a counter from the plurality of counters for the first attribute determine to correspond to the second attribute; and assigning, by the data processing system, using the counter, the fifth segment of the second system identifier for the dataset of the experiment.

18. The method of claim 15, further comprising:

determining, by the data processing system, responsive to receipt of the dataset of the experiment, that a plurality of attributes identified by a first system identifier including at least one of the source entity, the subject, the biological sample, the aliquot, and the dataset, matches a plurality of attributes derived from the dataset; and restricting, by the data processing system, responsive to the determination, generation of a second system identifier for the dataset using the plurality of attributes derived from the dataset of the experiment.

19. The method of claim 15, further comprising:

receiving, by the data processing system, from a client device, a query for records identifying one or more attributes of a plurality of attributes, the plurality of attributes including the source entity, the subject, the biological sample, the aliquot, and the experiment;

providing, by the data processing system, from a plurality of records maintained on the database, a subset of records corresponding to the one or more attributes as identified in the query for records to the client device.

20. The method of claim 15, further comprising providing, by the data processing system, a graph element using at least one of the plurality of system identifiers, the graph element including a plurality of nodes and a plurality of edges to connect the plurality of nodes, the plurality of nodes corresponding to a plurality of attributes, the plurality of edges corresponding to associations among the plurality of attributes.

* * * * *